US00PP11762P2

(12) United States Plant Patent
Rother

(10) Patent No.: US PP11,762 P2
(45) Date of Patent: Feb. 6, 2001

(54) DIMORPHOTHECA PLANT NAMED 'ROSE'

(76) Inventor: Reinhard W. Rother, 56 Emerald Monbulk Road, Emerald, Victoria, 3782 (AU)

( * ) Notice: Under 35 U.S.C. 154(b), the term of this patent shall be extended for 0 days.

(21) Appl. No.: 09/257,095

(22) Filed: Feb. 22, 1999

(51) Int. Cl.[7] ..... A01H 5/00
(52) U.S. Cl. ..... Plt./263
(58) Field of Search ..... Plt./263, 360

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Dimorphotheca plant name 'Rose', characterized by its low, compact, mounding and outwardly spreading growth habit; numerous leaves; upright inflorescences on long peduncles; freely branching habit; dark pink-colored ray florets contrasted with purple anthers and styles; numerous inflorescences per plant; and tolerance to high temperatures.

1 Drawing Sheet

BACKGROUND OF THE INVENTION

The present invention relates to a new and distinct cultivar of Dimorphotheca plant, botanically known as *Dimorphotheca aurantiaca* and referred to by the cultivar name 'Rose'.

The new cultivar is a product of a planned breeding program conducted by the Inventor in Emerald, Victoria, Australia. The objective of the breeding program was to create new compact Dimorphotheca cultivars with interesting ray floret colors and high temperature tolerance.

The new cultivar originated from a cross made by the Inventor in 1992 of a proprietary selection of *Dimorphotheca aurantiaca* identified as 90/78 as the female, or seed, parent and a proprietary selection of *Dimorphotheca aurantiaca* identified as 91/179 as the male, or pollen, parent. The new Dimorphotheca was selected by the Inventor as a flowering plant within the progeny of this cross in a controlled environment in Emerald, Victoria, Australia in 1992.

Plants of the new cultivar are different from plants of the female parent, the selection 90/78 in plant habit, infloresence size and floret color.

Plants of the new Dimorphotheca are different from plants of the male parent, the selection 91/179 in stem length and floret color.

Asexual propagation of the new cultivar by terminal cuttings and by tissue culture at Emerald, Victoria, Australia, has shown that the unique features of this new Dimorphotheca are stable and reproduced true to type in successive generations.

SUMMARY OF THE INVENTION

The following traits have been repeatedly observed and are determined to be the unique characteristics of 'Rose'. These characteristics in combination distinguish 'Rose' as a new and distinct cultivar:

1. Low, compact, mounding and outwardly spreading growth habit.
2. Numerous leaves and upright inflorescences on long peduncles.
3. Freely branching.

4. Dark pink-colored ray florets contrasted with purple anther sand styles.
5. Numerous inflorescences per plant.
6. Relatively tolerant to high temperatures.

Plants of the new cultivar differs from its sibling cultivar 'Mauve' (disclosed in U.S. Plant patent application Ser. No. 09/257,094) in growth rate, leaf size, leaf shape and ray floret color.

The new cultivar can be compared to the Osteospermum cultivar 'Mira', disclosed in U.S. Plant Pat. Ser. No. 11,082. However in side-by-side comparisons conducted in Emerald, Victoria, Australia, plants of the new cultivar are much more compact, have smaller inflorescences and ray florets are lighter in color.

The cultivar 'Rose' has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of a typical flowering plant of 'Rose'.

The photograph at the bottom of the sheet is close-up view of lower and upper surfaces of typical inflorescences (top) and upper and lower surfaces of typical leaves (bottom) of 'Rose'. Foliage and floret colors in the photographs may appear different from the actual colors due to light reflectance.

DETAILED BOTANICAL DESCRIPTION

The following observations, measurements and values describe a one-gallon container with three plants of the new cultivar grown in Bonsall, Calif., under outdoor, full-sun conditions with day temperatures ranging from 18 to 35° C. and night temperatures ranging from 13 to 18° C.

Color references are made to The Royal Horticultural Society Colour Chart except where general terms of ordinary dictionary significance are used.

Botanical classification: *Dimorphotheca aurantiaca* cultivar 'Rose'.

Parentage:

*Female, or seed, parent*.—Proprietary selection of *Dimorphotheca aurantiaca* identified as 90/78.

*Male, or pollen, parent*.—Proprietary selection of *Dimorphotheca aurantiaca* identified as 91/179.

Propagation:

*Type*.—By terminal cuttings.

*Time to initiate roots*.—Summer: About 12 to 15 days at 22° C. Winter: About 15 days at 22° C.

*Time to develop roots*.—About 30 days at 22° C.

*Root description*.—Thick; freely branching.

Plant description:

*Appearance*.—Perennial herbaceous container and garden plant. Broad inverted triangle. Low, compact, mounding and outwardly spreading growth habit. Compact with dense foliage and erect flower stems. Freely branching with about 7 lateral branches; removal of terminal apices (pinching) is usually not required.

*Crop time*.—About 8 to 12 weeks are required to produce a finished, flowering plant in a 10-cm container.

*Vigor*.—Low to moderate.

*Plant height*.—About 19 cm.

*Plant spread*.—About 16 cm.

*Lateral branch description*.—Length: About 15 to 21 cm. Diameter: About 5 mm. Internode length: About 5 to 10 mm. Texture: Sparsely pubescent. Color: 145B.

*Foliage description*.—Leaves alternate, single. Quantity of leaves per lateral branch: Numerous, about 20. Length, fully expanded leaves, basal: About 7 to 8.5 cm. Width, fully expanded leaves, basal: About 2.2 cm. Shape: Elliptic; minute irregular points along margin. Apex: Broadly acute. Base: Attenuate, sessile. Margin: Entire with widely-spaced minute teeth. Aspect: Mostly flat. Texture: Leathery with very fine pubescence on both surfaces, rough. Color: Young foliage, upper surface: 137A. Young foliage, lower surface: 137B. Fully expanded foliage, upper surface: 137A. Fully expanded foliage, lower surface: 137B. Attenuated leaf base: 144D. Venation, upper surface: 138C. Venation, under surface: 137D.

Inflorescence description:

*Appearance*.—Daisy-type composite inflorescence form. Inflorescences displayed above foliage, upright on long peduncles arising from leaf axils. Disc and ray florets arranged acropetally on a capitulum. Typically about 16 opened inflorescences per plant. Inflorescences last about one week. Inflorescences persistent.

*Flowering response*.—Plants flower continously from April to October in the Northern Hemisphere.

*Fragrance*.—None detected.

*Inflorescence size*.—Diameter: About 4.5 cm. Depth (height): About 1.5 cm. Diameter of disc: About 9 mm.

*Inflorescence buds*.—Length: About 1.8 cm. Width: About 8 mm. Shape: Ovoid. Color: 198A.

*Ray florets*.—Length: About 2.5 cm. Width: About 5 mm. Shape: Ligulate. Apex: Tri-dentate, minute. Base: Attenuate, acute. Margin: Entire. Aspect: Nearly flat. Texture: Smooth. Number of ray florets per inflorescence: About 20 in a single whorl. Color: When opening, upper surface: 75A. When opening, lower surface: 188A to 188B. Fully opened, upper surface: 82C. Fully opened, under surface: 194A, apex, 162A; dark purple central stripe; close to 183B.

*Disc florets*.—Shape: Tubular to salverform, five-lobed, fluted at apex. Number of disc florets per inflorescence: Numerous, about 75. Length: About 6 mm. Width: About 2 mm. Color: Immature: 4D. Mature: 4D; apex, 4A.

*Phyllaries*.—Shape: Elliptic to linear. Apex: Narrowly acute. Margin: Entire. Quantity and arrangement: About 20 per inflorescence; whorled. Texture: Coarse. Color: Upper surface: 143B. Lower surface: 143A.

*Peduncle*.—Length: About 11 cm. Aspect: Moderately strong, inflorescences held erect above foliage. Texture: Hispid; granular. Color: 144A to 144B.

*Reproductive organs*.—Androecium: Present on disc florets only. Stamens: Five. Anther shape: Oblong. Anther size: About 1 mm. Anther color: 86B. Pollen: Scarce. Pollen color: 6A. Gynoecium: Present on ray and disc florets. Pistils: One. Pistil length: About 5 mm. Stigma shape: Bipartite. Stigma color: 93A to 93B. Style length: About 4 mm. Style color: 155A. Ovary color: 145A.

Disease resistance: Resistance to pathogens common to Dimorphotheca has not been observed.

Weather tolerance: Plants of the new cultivar have been shown to be more tolerant to high temperatures than other Dimorphotheca cultivars known to the Inventor.

Seed production: Seed production has not been observed.

It is claimed:

1. A new and distinct cultivar of Dimorphotheca plant named 'Rose', as illustrated and described.

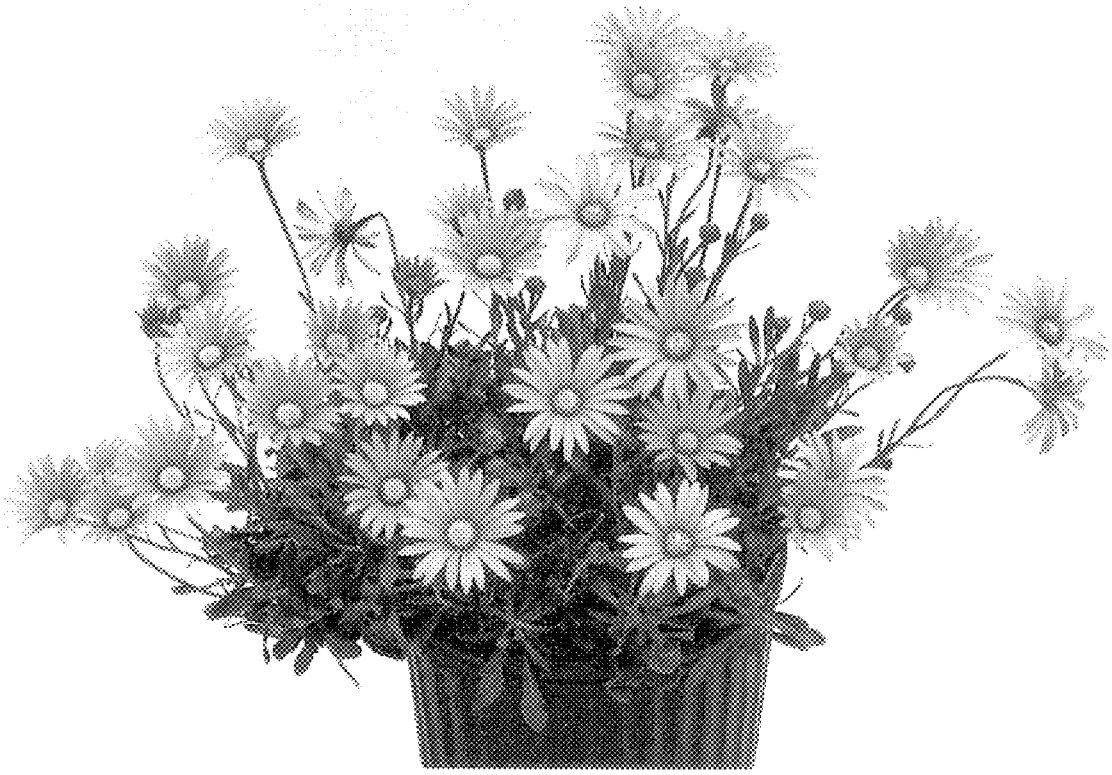
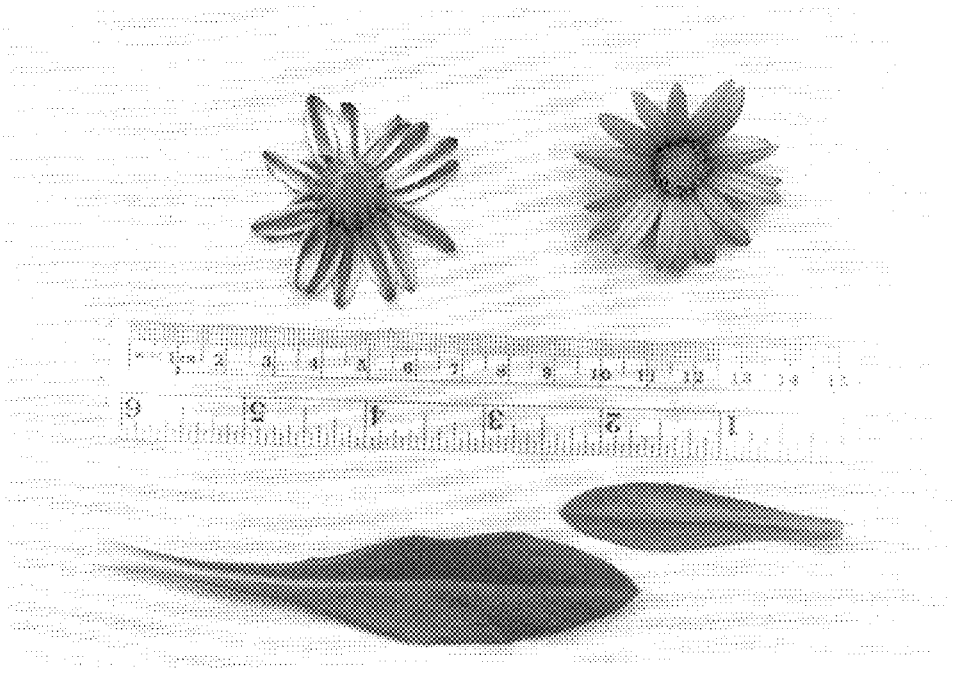

* * * * *